United States Patent [19]

Patarcity et al.

[11] Patent Number: 5,229,125
[45] Date of Patent: Jul. 20, 1993

[54] MOLLUSCICIDAL WATER DISTRIBUTION SYSTEM COMPONENTS

[75] Inventors: Adam J. Patarcity, Mt. Laurel, N.J.; David E. Newman, Holland, Pa.

[73] Assignee: Garlock Inc., New York, N.Y.

[21] Appl. No.: 789,267

[22] Filed: Nov. 8, 1991

[51] Int. Cl.$^5$ .................. A01N 25/34; C08L 23/06
[52] U.S. Cl. .................. 424/409; 424/406; 424/486; 514/772.4; 523/122
[58] Field of Search .......... 424/405, 78.09, 78.18, 424/406, 409, 486; 514/476, 478, 772.4; 523/122

[56] References Cited

U.S. PATENT DOCUMENTS

| | | | |
|---|---|---|---|
| 2,875,834 | 3/1959 | Shumard | 424/245 |
| 3,143,460 | 8/1964 | Pearce | 424/249 |
| 3,417,181 | 12/1968 | Cardarelli | 424/229 |
| 3,857,934 | 12/1974 | Bernstein et al. | 424/30 |
| 4,324,784 | 4/1982 | Naito et al. | 424/130 |
| 4,918,147 | 4/1990 | Yamamori et al. | 525/386 |
| 5,062,967 | 11/1991 | Muia et al. | 210/755 |
| 5,096,601 | 3/1992 | Muia et al. | 210/755 |

*Primary Examiner*—Thurman K. Page
*Assistant Examiner*—Neil S. Levy
*Attorney, Agent, or Firm*—Sixbey, Friedman, Leedom & Ferguson

[57] ABSTRACT

A polymer resin-molluscicidal composite for preventing and controlling damage to water distribution systems caused by *Dreissena polymorpha*, the zebra mussel, and other undesirable sessile mollusks is provided. The composite is preferably formed of an ultra-high molecular weight polyethylene and 0.1 to 20 weight percent of a water insoluble, high melting point molluscicide which is preferably a metal salt or complex of an organic sulfur compound. Alkyldithiocarbamates, tetraalkylthiuram sulfides and the metal salts and complexes thereof are preferred molluscicides. The molluscicidal composite may be formed into structural components, such as valves, or into linings, coatings and encapsulators.

8 Claims, No Drawings

MOLLUSCICIDAL WATER DISTRIBUTION SYSTEM COMPONENTS

TECHNICAL FIELD

The present invention relates generally to the prevention of sessile mollusk infestations in water distribution systems in contact with natural water sources and particularly to molluscicidal components for such systems.

BACKGROUND OF THE INVENTION

The spread of *Dreissena polymorpha*, the zebra mussel, to North America presents a classic example of how a foreign species of an organism can spread, unchecked by natural predators, to create major problems. *Dreissena polymorpha*, a sessile fresh water mollusk native to the Caspian Sea in Russia, is thought to have been transported to North American waters in about 1986 in the ballast of a ship. After its discharge into Lake St. Clair, the zebra mussel has multiplied rapidly and spread into all of the Great Lakes and many contiguous waterways as well, encrusting the hulls and engines of boats and the components of waterworks, cooling systems and other water distribution system structures in these waters. The tendency of this tenacious mollusk to form large colonies has created untold damage. There is currently no safe, effective and reliable way to prevent, or even control, the unwanted spread and biofouling produced by the zebra mussel.

A female zebra mussel produces about 30,000 eggs annually. When the eggs have been fertilized, they hatch into microscopic larvae which are carried randomly by currents until they mature sufficiently to attach to whatever hard surfaces they happen to contact. Once a zebra mussel larva fastens itself to a hard surface, the maturation process is completed, and each mature mussel has formed a hard hinged shell. The mussel then remains sessile in this location for the rest of its life. Zebra mussels will attach to virtually any hard underwater surface and are especially adherent to the shells of other zebra mussels. Consequently, large clumps of zebra mussels are quickly formed on surfaces where only one or a small number of larvae had originally attached.

The zebra mussel, which has a characteristic arrangement of dark and light brown stripes on its shell, attaches itself to firm objects by thread-like tentacles. These tentacles are tough fibers of a horny material and are known as byssal threads or byssuses. The byssal threads secrete an adhesive which enables the mussel to affix itself to any surface, no matter what its orientation relative to the horizontal. As a result, zebra mussels have attached themselves to pipes, valving, cooling equipment, intake and outflow lines and other components of such water distribution systems as municipal water treatment systems, industrial water systems, power plant cooling systems, and even those of marine vessels. Colonies of zebra mussels which can quickly reach a population density of 30,000 mussels per square meter, present substantial and significant problems to these systems.

The growth of zebra mussel colonies in pipes and other conduits in contact with fresh water sources reduces the effective bore of the conduits and increases the roughness factor, thus diminishing their water carrying capacity. In addition, by creating local differences in the oxidation state on the inner surface of cast iron and steel pipes, zebra mussel colonies can promote electro-corrosion of these pipes. At least one municipality whose water supply comes from one of the Great Lakes has had its municipal water supply cut off because the intake lines were clogged with zebra mussel colonies. Industrial plants have had the flow of essential cooling water interrupted by zebra mussel infestations.

Zebra mussel colonies threaten virtually every municipality, industry and utility that draws water from the rivers, lakes and streams where these organisms have spread. Because the motile zebra mussel larvae forms range from microscopic to very tiny in size they are easily drawn through water intake screens and other components and deep inside water treatment or cooling systems. Once inside these systems, the immature mussels can lodge anywhere, and form bio-fouling colonies.

Once the magnitude of the zebra mussel population explosion in North America was fully appreciated, efforts to prevent and control this pest were proposed. Because *Dreissena polymorpha* has no natural predators in these waters, eradication of the mussels has focused primarily on manually scraping the colonies from intake pipes and other equipment. However, this method is slow, expensive and does not guarantee the removal of every mussel. Additionally, the equipment being scraped cannot be used and must be out of service until mussel removal has been completed. Although many European water distribution systems employ dual water intake lines so one can be used while the other is shut down for zebra mussel removal, this is not an inexpensive modification for an existing water distribution system.

Because the zebra mussel veliger larvae forms do not survive at temperatures below about 13° C., it has been suggested that water intake and other equipment be located at water depths where the temperature is not likely to rise above 13° C. However, this is not always possible. Even where it is feasible, it could be quite costly to relocate existing system components.

The application of up to 50 ppm chlorine to water where zebra mussel removal is required for a period of about two weeks has been proposed, and appears to be a reliable control method. However, the potential toxicity of the chlorine concentrations required to eradicate mussels to other animals and humans and the undesirable chlorinated organic compounds formed by chlorine are major disadvantages to this method. Moreover, chlorine can be quite corrosive to water distribution system operating components.

Other chemical methods have been proposed to combat zebra mussels and harmful marine mollusks. For example, U.S. Pat. No. 4,154,818 to Kanada et al. discloses a gel product containing a molluscicide for exterminating such harmful marine mollusks as Teredo, *Mytilis edulis*, barnacles and Hydrozoa which tend to adher to vessel walls and other surfaces. The gel product is suspended in a mesh container or the like in the water near the infestation, and the molluscicide gradually dissolves. Although this method should eradicate an infestation of mollusks in the vicinity of the gel, the concentration of the molluscicide in the vicinity of the gel is not subject to precise control, but is dependent on water conditions and could be high enough to be toxic to desirable organisms as well as the mollusks to be exterminated.

U.S. Pat. No. 5,015,395 to Muia et al. discloses a method for controlling zebra mussels in aqueous systems by adding to the system a water soluble dialkyl diallyl quaternary ammonium polymer. This compound, while apparently effective in killing zebra mussels, also effectively kills other aquatic life if the concentration is not precisely controlled.

U.S. Pat. No. 5,040,487 to Bollyky et al. discloses a method of controlling zebra mussel infestations in waterworks by introducing ozone into the water entering the system as close to the crib of the water intake as possible. Additional applications are required if the water line is long or the system is complex. This method requires the relatively precise application of ozone from a separate ozone source to be effective. Additionally, it is most effective against eggs and larvae forms, and will only kill immature mussels before they have attached to a surface.

It has also been proposed to selectively eradicate zebra mussels with potassium by adding potassium to paint applied to underwater structures since potassium is apparently toxic to zebra mussels. While this may be promising, its efficacy has yet to be demonstrated.

The prior art, therefore has failed to provide a safe, reliable method or apparatus for preventing the damage caused by zebra mussel or other undesirable sessile mollusk infestations to water distribution systems with components which contact bodies of fresh water infested with zebra mussels or undesirable sessile mollusks that does not require the application to the water of a chemical that is potentially toxic to other aquatic life.

SUMMARY OF THE INVENTION

It is a primary object of the present invention, therefore, to overcome the disadvantages of the prior art and to provide a means for preventing and controlling damage due to infestations of zebra mussels and other undesirable aquatic sessile mollusks in water distribution systems in contact with bodies of water containing these mollusks.

It is another object of the present invention to provide a method for preventing and controlling zebra mussel infestations that does not require the application of potentially toxic chemicals to the bodies of water where control or prevention of the zebra mussels is desired.

It is still another object of the present invention to provide a component for a water treatment, cooling or other system in contact with a body of water infested by harmful or undesirable sessile mollusks which prevents the attachment of the mollusks to the component.

It is yet another object of the present invention to provide a molluscicidal composite suitable for coating, lining or fabricating water distribution system components.

It is a further object of the present invention to provide a molluscicidal plastic component for a water distribution system.

It is a still further object of the present invention to provide apparatus for preventing the biofouling of water intakes and valving associated with water distribution systems located in areas with an abundance of mollusks.

The foregoing objects are satisfied by providing a molluscicidal composite comprising a hydrocarbon polymer and a substantially water insoluble molluscicidal agent. The molluscicidal composite, which is preferably formed of ultra-high molecular weight polyethylene and a high melting point organic sulfur compound with molluscicidal activity, may be used to line, coat or encapsulate water distribution system components or to form a component of a water distribution system. The composite of the present invention effectively prevents the attachment of sessile mollusks, such as *Dreissena polymorpha*, or zebra mussels, to the surfaces of the components formed of or coated, lined or encapsulated with this composite.

Other objects and advantages will be apparent from the following description and claims.

DESCRIPTION OF THE PREFERRED EMBODIMENTS

Since its introduction into North American waters, the zebra mussel (*Dreissena polymorpha*) has spread at a phenomenal rate so that this organism is now found in all of the Great Lakes and in some of the river basins connected to the Great Lakes. Unless this infestation is checked, the zebra mussel could spread to virtually every body of water in North America.

In most of the United States and Canada zebra mussel reproduction is seasonal, since the veliger larvae require water temperatures above about 13° C. to survive, and do not develop well at temperatures greater than about 37° C. Optimum temperatures for veliger larvae development are between about 20° and 22° C. Unlike available control methods which apply molluscicidal agents directly to the water surrounding the critical components of the water distribution system and, therefore, require at least some monitoring of the water temperature to ensure that the application of the molluscicidal agent is likely to be effective, the molluscicidal activity of the present invention is available at all times. Moreover, the present invention avoids killing or injuring other aquatic organisms, and does not add polluting substances to the water, which is usually unavoidable with known molluscicidal methods and compositions.

The present invention is described primarily with respect to the prevention and control of zebra mussels. However, it is equally applicable to the prevention and control of infestations of other undesirable aquatic sessile mollusks.

The inventors of the present invention have discovered that the incorporation of a substantially water insoluble molluscicidal agent into the ultra-high molecular weight hydrocarbon polymers used to form components and surfaces of water distribution systems effectively prevents the attachment of zebra mussels to these surfaces.

Many valves and other components available for use in water distribution systems, particularly those used by the electric power generating industry, have recently been fabricated from or lined with polymers. Ultra-high molecular weight polyethylene (UHMWPE) has been the preferred material for this purpose because it provides a smooth, substantially chemically inert, surface with outstanding abrasion resistance. However, even this material, which was thought to be too smooth for zebra mussel attachment, has provided a place to lodge and attach for these tenacious creatures. The creation of a surface antagonistic to zebra mussel attachment and growth required the addition of a molluscicidal agent to the polymer.

It was discovered that a molluscicide with a melting point of at least 300° F. or around the processing temperature for the polymer resin to be used in forming the selected component or surface can be dry blended in particle form into the resin. The molluscicide-resin blend is heated to the melting point and then molded or formed by conventional compression molding or forming methods. The molded or formed product can be machined into the configurations required to produce valve components, water inlet linings and the like. The molluscicidal agent and polymer resin mixture can also be processed according to conventional methods to form coatings.

The hydrocarbon polymer resin preferred for forming the components, linings, coatings and other structures according to the present invention is ultra-high molecular weight polyethylene or polypropylene. These resins produce water distribution system components which are durable and long-lasting. However, other polymer resins able to withstand the environment characteristic of systems in contact with bodies of water populated by zebra mussels or other undesirable mollusks could also be used.

Commercially available molluscicidal agents were evaluated and tested for the efficacy in preventing zebra mussel attachment when blended with a hydrocarbon polymer resin to form a composite. Potential molluscicidal agents were reviewed for their commercial availability, biocidal or repellant activity, high melting point (preferably over 300° F.), high thermal stability, compatibility or solubility in hydrocarbon polymers and very low solubility in water. The ideal molluscicidal agent should exert its exterminating action in a very small dosage with little or no toxicity to other forms of life.

Following a review of several potential molluscicides, the following group was selected for having met the criteria listed above: metallic copper, zinc bis (dimethyldithiocarbamate), copper stearate and triphenyl tin hydroxide. The organic sulfur compounds known as tetraalkylthiuram disulfides and tetraalkylthiuram monosulfides and their metal salts and complexes were also determined to be suitable for this purpose.

The level of addition of the molluscicide to the composite should be within the range of 0.1 to 20 weight percent of the resin.

Samples of composites formed from ultra-high molecular weight polyethylene (UHMWPE) and the foregoing molluscicides were prepared to test their resistance to zebra mussel attachment. The molluscicides were added to UHMWPE resin at levels of 0.5, 2.0 and 5.0 weight percent, and a sample water distribution system component was formed. A control component was formed of UHMWPE resin to which no molluscicide had been added. The sample components thus formed were immersed at various sites in Lake Erie with known zebra mussel infestations. The samples were left in place for about five months.

When the samples were removed from Lake Erie at the conclusion of the test period, which extended from May to October, normally the peak mussel season, the control sample showed zebra mussel attachment. In addition, the UHMWPE resin-molluscicide samples containing metallic copper, copper stearate and triphenyl tin hydroxide all exhibited varying degrees of zebra mussel attachment. The samples formed from a composite of UHMWPE resin and organic sulfur compounds were free from zebra mussel attachment at all of the additive levels tested.

In addition to the immersion study, samples containing 5.0 weight percent zinc bis (dimethyldithiocarbamate) were subjected to water extraction testing to determine whether zinc bis (dimethyldithiocarbamate) was likely to have been extracted from the samples while they were immersed in Lake Erie. The extraction tests indicated that some zinc, which formed zinc hydroxide or similar compounds, rather than zinc bis (dimethyldithiocarbamate), would have left the resin-molluscicide composite components while they were submerged in Lake Erie. However, the zinc extracted from the molluscicidal composites tested was on the order of 0.2 parts per trillion in the test water surrounding these composites. Consequently, the molluscicidal-resin composites of the present invention, unlike prior art zebra mussel control methods, will not add potential pollutants to the water.

The molluscicidal polymer resin composite of the present invention can be fabricated into a variety of components for use in water distribution systems, such as those used by municipal water works, utilities, and industrial water systems. The molluscicidal polymer resin composite of the present invention can also be formed into internal liners for pipes, conduits, channels, water boxes and the like for such systems. In addition, the present molluscicidal composite can be made into coatings and encapsulators so that components formed of non-molluscicidal materials will repel attachment by zebra mussels and other undesirable sessile mollusks.

The precise mechanism by which the polymer resin-molluscicidal composite of the present invention prevents the zebra mussel from attaching to surfaces formed of the composite is not fully understood. It is thought that even extremely dilute concentrations of the molluscicide, for example on the order of several parts per billion, is sufficient to prevent larval metamorphosis when ingested by the zebra mussel larva. It is also likely that the byssal threads found in the more mature mussel do not adher to a molluscicide-containing surface. Whatever the exact inhibitory method, the polymer resin-molluscicidal composites of the present invention effectively prevent the attachment of zebra mussels to surfaces containing them and, therefore, provide an effective means for preventing damage to water distribution systems typically associated with zebra mussel infestations.

INDUSTRIAL APPLICABILITY

The polymer resin-molluscicide composites of the present invention will find their primary application in the formation of structural components, linings and coatings for structures in contact with bodies of water known to be infested with zebra mussels or other undesirable sessile mollusks. Municipal water systems, power generating plants, industrial facilities and other users that draw and use water from sources where these mollusks are found will find the present invention especially useful in preventing the problems that arise from their unchecked spread.

We claim:

1. A structural material useful for forming structural components of water distribution systems that remain free from zebra mussel attachment in aquatic environments infested with zebra mussels, wherein said structural material comprises ultra-high molecular weight polyethylene having distributed throughout a substantially water insoluble molluscicide selected from the group consisting of organic sulfur compounds having a melting point of at least 300° F. and the metal salts and complexes thereof.

2. The structural material of claim 1, wherein 0.1 to 20.0 weight percent of said molluscicide is distributed throughout said ultra-high molecular weight polyethylene.

3. The structural material of claim 1, wherein said molluscicide is selected from the group consisting of dialkyldithiocarbamate metal salts and tetraalkylthiuram sulfides.

4. The structural material of claim 3 wherein said molluscicide is zinc bis (dimethyldithiocarbamate).

5. A valve component for a water distribution system formed from the structural material of claim 1.

6. A water inlet lining for a water distribution system formed from the structural material of claim 1.

7. A water conduit for use in aquatic environment formed from the structural material of claim 1.

8. The structural material of claim 1, wherein said polyethylene contains distributed throughout 0.1 and 20.0 weight percent of zinc bis (dimethyldithiocarbamate).

* * * * *